(12) United States Patent
Kato et al.

(10) Patent No.: US 6,344,119 B2
(45) Date of Patent: *Feb. 5, 2002

(54) GAS SENSOR

(75) Inventors: Nobuhide Kato, Ama-gun; Kunihiko Nakagaki, Nagoya, both of (JP)

(73) Assignee: NGK Insulators, Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/025,814

(22) Filed: Feb. 19, 1998

(30) Foreign Application Priority Data

Mar. 27, 1997 (JP) .............................. 9-075947

(51) Int. Cl.[7] .......................................... G01N 27/407
(52) U.S. Cl. ..................... 204/425; 204/426; 204/427; 205/781
(58) Field of Search ................. 204/421–429

(56) References Cited

U.S. PATENT DOCUMENTS

| | | | |
|---|---|---|---|
| 4,810,350 A | | 3/1989 | Mantese et al. |
| 5,108,577 A | * | 4/1992 | Mase et al. ................. 204/426 |
| 5,662,786 A | * | 9/1997 | Friese ....................... 204/429 |
| 5,763,763 A | * | 6/1998 | Kato et al. ................. 204/429 |
| 5,879,525 A | * | 3/1999 | Kato ......................... 204/424 |

FOREIGN PATENT DOCUMENTS

| | | |
|---|---|---|
| DE | 4401749 | 7/1994 |
| EP | 0310206 | 4/1989 |
| EP | 0443259 | 8/1991 |
| EP | 0678740 | 10/1995 |
| EP | 0798556 | 10/1997 |
| JP | 4-26055 | 6/1985 |
| JP | 5-62297 | 6/1985 |
| WO | WO 95/30146 | 11/1995 |

* cited by examiner

Primary Examiner—T. Tung
(74) Attorney, Agent, or Firm—Parkhurst & Wendel, L.L.

(57) ABSTRACT

It is intended to avoid invasion of oxygen through any route except for an introducing port for a measurement gas so that the amount of oxide or inflammable gas contained in the measurement gas may be measured highly accurately. Insulative layers are provided for respective lead wires at positions corresponding to portions at which the temperature of the oxygen ion-conductive solid electrolyte is increased due to heat generation effected by a heater. Each of the insulative layers is formed to have a pattern in which one end is exposed to a first chamber or a second chamber, and the other end terminates at a position separated by a predetermined distance from a corresponding through-hole. At least the lead wires, which lead to an auxiliary pumping electrode and a detecting electrode, are densified. Preferably, the insulative layers for these lead wires are also densified.

3 Claims, 11 Drawing Sheets

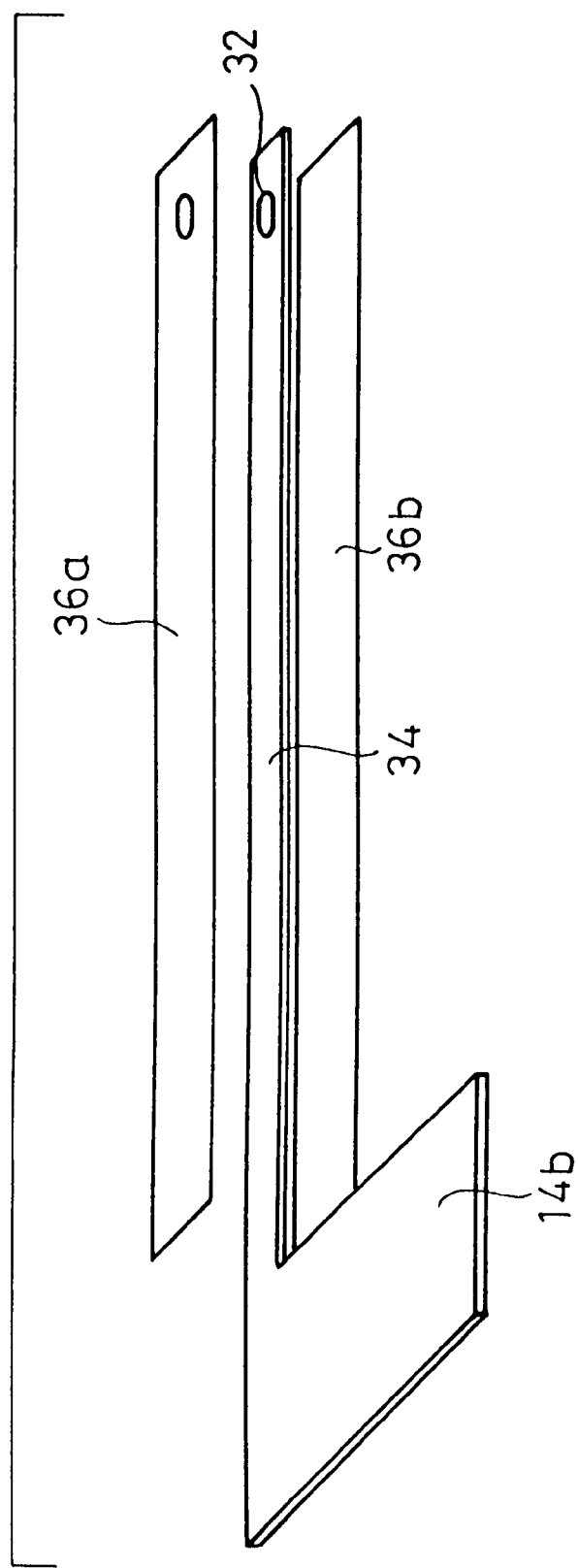

GAS SENSOR

BACKGROUND OF THE INVENTION

1. Field of the Invention

The present invention relates to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as $H_2$, CO, and hydrocarbon (CnHm). Preferably, the present invention relates to a gas sensor for measuring NO and $NO_2$.

2. Description of the Related Art

Exhaust gas, which is discharged from vehicles or automobiles such as gasoline-fueled automobiles and diesel powered automobiles, contains nitrogen oxides (NOx) such as nitrogen monoxide (NO) and nitrogen dioxide ($NO_2$), as well as carbon monoxide (CO), carbon dioxide ($CO_2$), water ($H_2O$), hydrocarbon (CnHm), hydrogen ($H_2$), oxygen ($O_2$) and so on. In such exhaust gas, about 80% of the entire NOx is occupied by NO, and about 95% of the entire NOx is occupied by NO and $NO_2$.

The three way catalyst, which is used to clean HC, CO, and NOx contained in the exhaust gas, exhibits its maximum cleaning efficiency in the vicinity of the theoretical air fuel ratio (A/F=14.6). If A/F is controlled to be not less than 16, the amount of produced NOx is decreased. However, the cleaning efficiency of the catalyst is lowered, and consequently the amount of discharged NOx is apt to increase.

Recently, in order to effectively utilize fossil fuel and avoid global warming, the market demand increases, for example, in that the discharge amount of $CO_2$ should be suppressed. In order to respond to such a demand, it becomes more necessary to improve the fuel efficiency. In response to such a demand, for example, the lean burn engine and the catalyst for cleaning NOx are being researched. Especially, the need for a NOx sensor increases.

A conventional NOx analyzer has been hitherto known in order to detect NOx as described above. The conventional NOx analyzer is operated to measure a characteristic inherent in NOx, based on the use of chemical luminous analysis. However, the conventional NOx analyzer is inconvenient in that the instrument itself is extremely large and expensive. The conventional NOx analyzer requires frequent maintenance because optical parts are used to detect NOx. Further, when the conventional NOx analyzer is used, any sampling operation should be performed for measurement of NOx, wherein it is impossible to directly insert a detecting element itself into a fluid. Therefore, the conventional NOx analyzer is not suitable for analyzing transient phenomena such as those occur in the exhaust gas discharged from an automobile, in which the condition frequently varies.

In order to dissolve the inconveniences as described above, there has been suggested a sensor for measuring a desired gas component in exhaust gas by using a substrate composed of an oxygen ion-conductive solid electrolyte.

FIG. 10 shows a cross-sectional arrangement of a gas analyzer disclosed in International Publication WO 95/30146. This apparatus comprises a first chamber 4 for introducing a measurement gas containing NO through a small hole 2 thereinto, and a second chamber 8 for introducing the measurement gas from the first chamber 4 through a small hole 6. Wall surfaces for constructing the first chamber 4 and the second chamber 8 are composed of zirconia ($ZrO_2$) partition walls 10a, 10b through which oxygen ion is transmittable. A pair of measuring electrodes 12a, 12b, 14a, 14b for detecting the partial pressure of oxygen in the respective chambers are disposed on one of the $ZrO_2$ partition walls 10a of the first chamber 4 and the second chamber 8 respectively. Pumping electrodes 16a, 16b, 18a, 18b for pumping out $O_2$ in the respective chambers to the outside of the chambers are disposed on the other $ZrO_2$ partition wall 10b respectively.

In the gas analyzer constructed as described above, the partial pressure of oxygen contained in the measurement gas G introduced into the first chamber 4 via the small hole 2 is detected by a voltmeter 20 as a difference in electric potential generated between the measuring electrodes 12a, 12b. A voltage in a range of 100 to 200 mV is applied between the pumping electrodes 16a, 16b by the aid of a power source 22 so that the difference in electric potential has a predetermined value. Accordingly, $O_2$ in the first chamber 4 is pumped out to the outside of the apparatus. The amount of oxygen pumped out as described above can be measured by using an ammeter 24.

On the other hand, the measurement gas G, from which almost all of $O_2$ has been removed, is introduced into the second chamber 8 via the small hole 6. In the second chamber 8, a difference in electric potential, which is generated between the measuring electrodes 14a, 14b, is detected by using a voltmeter 26. Thus, the partial pressure of oxygen in the second chamber 8 is measured. Further, NO contained in the measurement gas G introduced into the second chamber 8 is decomposed as follows by the aid of the voltage applied between the pumping electrodes 18a, 18b by means of a power source 28:

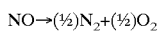

$O_2$ is generated during this process, which is pumped out to the outside of the chamber by the aid of the pumping electrodes 18a, 18b. At this time, a generated current value is detected by using an ammeter 30. Thus, the concentration of NO contained in the measurement gas G is measured.

In the case of the gas analyzer constructed as described above, the partial pressure of oxygen in the chamber is adjusted by measuring the minute voltage between the measuring electrodes 12a, 12b and between the measuring electrodes 14a, 14b, and the concentration of NO contained in the measurement gas G is measured by measuring the minute current between the pumping electrodes 18a, 18b. In this case, in order to maintain the measurement accuracy in the gas analyzer, it is necessary to sufficiently ensure the insulation performance between lead wires connected to the respective measuring electrodes 12a, 12b, 14a, 14b and the pumping electrodes 18a, 18b so that the variation in detection signal due to cross talk and disturbance is avoided as less as possible.

In general, the insulation performance between the lead wires is ensured in accordance with such methods as disclosed, for example, in Japanese Patent Publication Nos. 4-26055 and 5-62297, in which a porous insulative material is used to make insulation between the pumping cell and the sensor cell or make insulation between electrode lead wires. Those generally used as the material for ensuring the insulation performance as described above include alumina and spinel.

Further, in order to improve the pumping ability or improve the response performance when the electromotive force is measured, the respective electrodes used for the gas analyzer are produced by using porous materials. FIG. 11 shows an illustrative pattern of an electrode lead wire 34 which is wired from a through-hole 32 connected to an external connector to the measuring electrode 14b. In the illustrative arrangement shown in FIG. 11, porous insulative layers 36a, 36b are formed over and under the electrode lead wire 34 respectively to make insulation from other lead wires.

However, in the case of the conventional gas analyzer, the porous insulative layers 36a, 36b are formed to extend up to the through-hole 32. For this reason, a problem arises in that $O_2$, which makes invasion from the outside through the through-hole 32, invades the second chamber 8 through the insulative layers 36a, 36b, and it increases the oxygen concentration in the vicinity of the measuring electrode 14b disposed near to the insulative layers 36a, 36b.

Further, the electrode lead wire 34 is composed of a porous material. For this reason, a problem arises in that $O_2$ invades the second chamber 8 through the electrode lead wire 34 from the connector side of the electrode lead wire 34 which is exposed to the outside through the through-hole 32, and it increases the oxygen concentration in the vicinity of the connecting section of the measuring electrode 14b with respect to the electrode lead wire 34. Especially, the measuring electrode 14b for the second chamber 8 tends to be affected by $O_2$ having made the invasion. Therefore, an inconvenience arises in that the $O_2$ increases the NO decomposition current.

Usually, a porous electrode composed of Pt is used for the measuring electrode 14b disposed at the inside of the second chamber 8. However, the use of such an electrode involves the following problem. That is, $O_2$ gas is accumulated in the electrode lead wire 34 through the measuring electrode 14b, and the oxygen concentration in the vicinity of the measuring electrode 14b is increased upon the next pumping operation due to leakage of $O_2$ from the electrode lead wire 34.

When the oxygen concentration in the vicinity of the measuring electrode 14b is increased due to the invasion of $O_2$ into the second chamber 8 through the insulative layers 36a, 36b and the electrode lead wire 34 and due to the accumulation and leakage of $O_2$ from the electrode lead wire 34 as described above, then an inconvenience arises in that the pumping current, which would otherwise depend on the decomposition of NO, is increased, and it becomes impossible to measure NO highly accurately.

SUMMARY OF THE INVENTION

The present invention has been made in order to overcome the inconveniences described above, an object of which is to provide a gas sensor which makes it possible to avoid invasion of oxygen through any route except for an introducing port for a measurement gas so that the amount of oxide or inflammable gas contained in the measurement gas may be measured extremely highly accurately.

According to the present invention, there is provided a gas sensor comprising a main pumping means including an inner pumping electrode and an outer pumping electrode arranged on inner and outer surfaces of a substrate composed of an oxygen ion-conductive solid electrolyte, for pumping-processing oxygen contained in a measurement gas introduced from external space on the basis of a control voltage applied between the inner pumping electrode and the outer pumping electrode; an electric signal-generating conversion means including an inner detecting electrode and an outer detecting electrode arranged on inner and outer surfaces of a substrate composed of an oxygen ion-conductive solid electrolyte, for decomposing a predetermined gas component contained in the measurement gas after being pumping-processed by the main pumping means, by means of a catalytic action and/or electrolysis to make conversion into an electric signal corresponding to an amount of oxygen produced by the decomposition; and insulative layers and conductive layers formed on a plurality of solid electrolyte green sheets, the plurality of green sheets being stacked and integrated into one unit followed by being sintered; wherein at least a lead wire connected to the inner detecting electrode of the electric signal-generating conversion means, which is exposed to the measurement gas, is densified; and the predetermined gas component contained in the measurement gas is measured on the basis of the electric signal detected by the electric signal-generating conversion means.

According to the present invention, at first, the oxygen, which is contained in the measurement gas introduced from the external space, is pumping-processed by the main pumping means, and the oxygen is adjusted to have a predetermined concentration. The measurement gas, which has been adjusted for the concentration of oxygen by means of the main pumping means, is introduced into the electric signal-generating conversion means in the next step. The electric signal-generating conversion means decomposes the predetermined gas component contained in the measurement gas after being pumping-processed by the main pumping means, by means of the catalytic action and/or electrolysis to make conversion into the electric signal corresponding to the amount of oxygen produced by the decomposition. Thus, the predetermined gas component contained in the measurement gas is measured on the basis of the electric signal supplied from the electric signal-generating conversion means.

When the electric signal-generating conversion means comprises a measuring pumping means and a current-detecting means, the measurement gas, which has been adjusted for the oxygen concentration by means of the main pumping means, is introduced into the measuring pumping means.

The measuring pumping means decomposes the predetermined gas component contained in the introduced measurement gas in accordance with the catalytic action and/or electrolysis. The oxygen produced by the decomposition is pumping-processed on the basis of a measuring pumping voltage applied between the inner detecting electrode and the outer detecting electrode. The pumping current, which is generated in the measuring pumping means corresponding to the amount of oxygen pumping-processed by the measuring pumping means, is detected by the current-detecting means. Thus, the predetermined gas component is measured depending on the amount of oxygen.

Alternatively, when the electric signal-generating conversion means comprises a concentration-detecting means and a voltage-detecting means, the measurement gas, which has been adjusted for the oxygen concentration by the main pumping means, is introduced into the concentration-detecting means. The concentration-detecting means decomposes the predetermined gas component contained in the introduced measurement gas in accordance with the catalytic action. An electromotive force of the oxygen concentration cell is generated depending on a difference between the amount of oxygen produced by the decomposition and the amount of oxygen contained in a gas existing on the side of the outer detecting electrode. The electromotive force is detected by the voltage-detecting means. Thus, the predetermined gas component is measured depending on the amount of oxygen.

In the present invention, at least the lead wire, which is connected to the inner detecting electrode of the electric signal-generating conversion means (the inner detecting electrode of the measuring pumping means or the inner detecting electrode of the concentration-detecting means) exposed to the measurement gas, is densified. Accordingly, the gas sensor is prevented from invasion of unnecessary oxygen from the outside through the lead wire. As a result, the amount of the predetermined gas component can be measured highly accurately on the basis of only the oxygen obtained from the predetermined gas component.

In the gas sensor according to the present invention, the lead wire may be composed of a cermet comprising a ceramic and a metal of the platinum group. In this embodiment, it is preferable that the ceramic contained in the lead wire has a sintering degree which is equivalent to or not less than a sintering degree of the solid electrolyte substrate.

Especially, when the lead wire is composed of a cermet comprising $ZrO_2$ and a metal of the platinum group, it is preferable that $ZrO_2$ contained in the lead wire has a sintering degree which is equivalent to or not less than a sintering degree of $ZrO_2$ contained in the solid electrolyte substrate.

It is preferable that the lead wire has a porosity of not more than 10%. Further, it is preferable that the lead wire is in an insulated state which is maintained by using a densified insulative material.

The gas sensor according to the present invention may further comprise an auxiliary pumping means including an inner auxiliary electrode and an outer auxiliary electrode arranged on the inner and outer surfaces of the substrate composed of the oxygen ion-conductive solid electrolyte, for pumping-processing oxygen contained in the measurement gas after being pumping-processed by the main pumping means on the basis of an auxiliary pumping voltage applied between the inner auxiliary electrode and the outer auxiliary electrode.

Accordingly, the measurement gas, which has been firstly subjected to coarse adjustment for the predetermined gas component to have a predetermined concentration by the aid of the main pumping means, is further subjected to fine adjustment for the concentration of the predetermined gas component by the aid of the auxiliary pumping means.

In general, when the concentration of the predetermined gas component in the measurement gas in the external space is greatly changed (for example, when oxygen is changed from 0% to 20%), then the distribution of the concentration of the predetermined gas component in the measurement gas to be introduced into the main pumping means is greatly changed, and the amount of the predetermined gas component to be introduced into the measuring pumping means or the concentration-detecting means is also changed.

During this process, the oxygen concentration in the measurement gas after being pumping-processed by the main pumping means is finely adjusted in accordance with the pumping process effected by the auxiliary pumping means. However, owing to the pumping process performed by the main pumping means, the change in concentration of oxygen in the measurement gas introduced into the auxiliary pumping means is greatly reduced as compared with the change in concentration of oxygen in the measurement gas introduced from the external space (measurement gas introduced into the main pumping means). Accordingly, it is possible to accurately and constantly control the concentration of the predetermined gas component in the vicinity of the inner detecting electrode of the measuring pumping means or in the vicinity of the outer detecting electrode of the concentration-detecting means.

Therefore, the concentration of the predetermined gas component introduced into the measuring pumping means or the concentration-detecting means is scarcely affected by the change in concentration of oxygen in the measurement gas (measurement gas introduced into the main pumping means). As a result, the pumping current value detected by the current-detecting means or the electromotive force detected by the voltage-detecting means is not affected by the change in oxygen concentration in the measurement gas, which has a value accurately corresponding to the amount of the objective component existing in the measurement gas.

It is preferable to densify the lead wire and/or the insulative layer concerning the inner auxiliary pumping electrode, for the purpose of accurate control of the oxygen concentration in the measurement gas.

The above and other objects, features, and advantages of the present invention will become more apparent from the following description when taken in conjunction with the accompanying drawings in which a preferred embodiment of the present invention is shown by way of illustrative example.

DESCRIPTION OF THE DRAWINGS

FIG. 11 illustrates the form of construction of the electrode lead wire and the insulative layer in the gas analyzer concerning the conventional technique.

DESCRIPTION OF THE PREFERRED EMBODIMENT

Explanation will be made below with reference to FIGS. 1 to 9 for several illustrative embodiments in which the gas sensor according to the present invention is applied to gas sensors for measuring oxides such as NO, $NO_2$, $SO_2$, $CO_2$, and $H_2O$ contained in, for example, atmospheric air and exhaust gas discharged from vehicles or automobiles, and inflammable gases such as $H_2$, CO, and CnHm.

Figure 1:
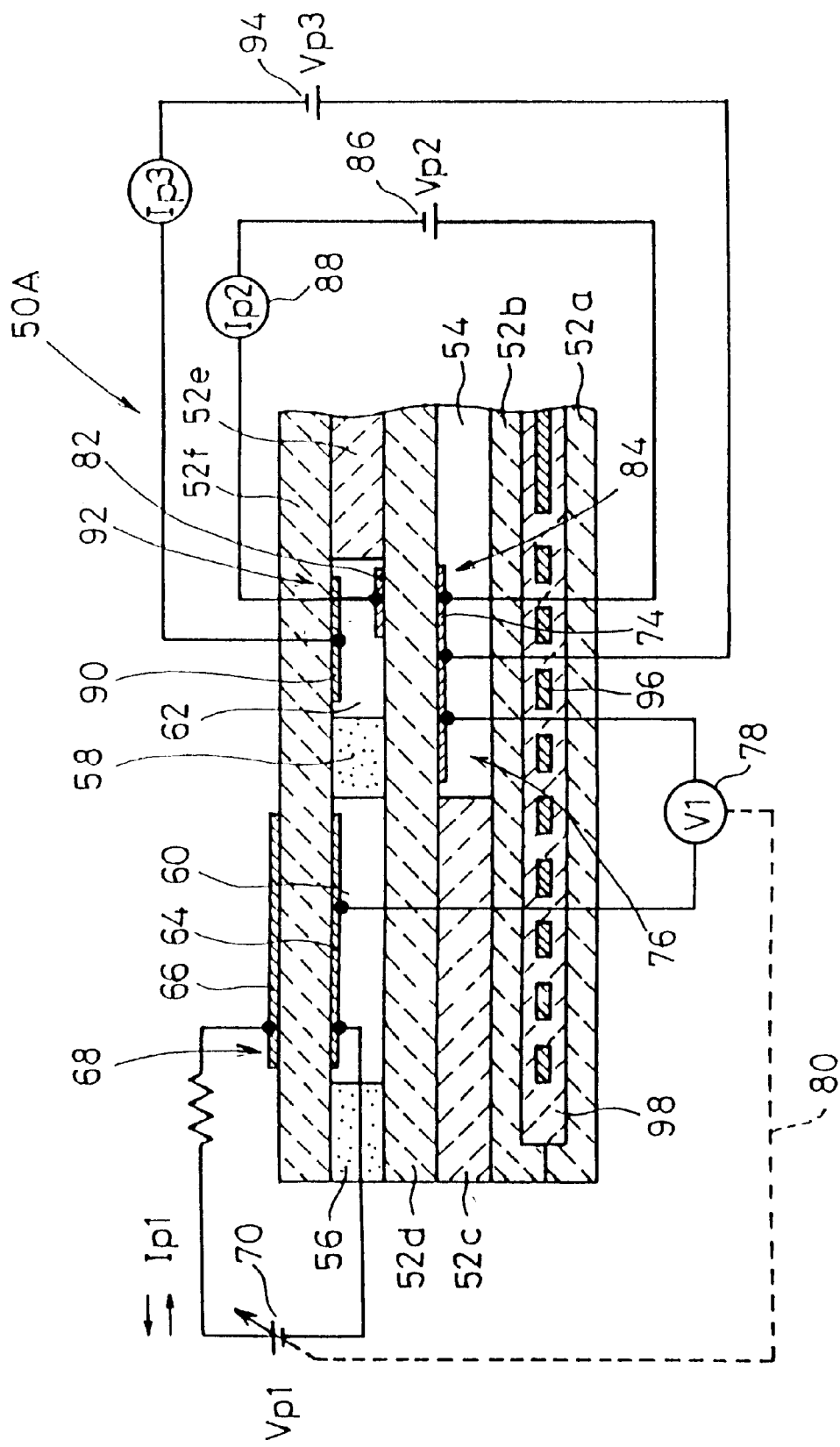
FIG. 1 shows a cross-sectional view illustrating an arrangement of a gas sensor according to a first embodiment.

At first, as shown in FIG. 1, a gas sensor 50A according to the first embodiment is generally constructed to have a lengthy plate-shaped configuration as a whole, comprising, for example, six stacked solid electrolyte layers 52a to 52f composed of ceramics based on the use of oxygen ion-conductive solid electrolytes such as $ZrO_2$. First and second layers from the bottom are designated as first and second substrate layers 52a, 52b respectively. Third and fifth layers from the bottom are designated as first and second spacer layers 52c, 52e respectively. Fourth and sixth layers from the bottom are designated as first and second solid electrolyte layers 52d, 52f respectively.

Specifically, the first spacer layer 52c is stacked on the second substrate layer 52b. The first solid electrolyte layer 52d, the second spacer layer 52e, and the second solid electrolyte layer 52f are successively stacked on the first spacer layer 52c.

A space (reference gas-introducing space) 54, into which a reference gas such as atmospheric air to be used as a reference for measuring a predetermined gas component is introduced, is formed between the second substrate layer 52b and the first solid electrolyte layer 52d, the space 54 being comparted by a lower surface of the first solid electrolyte layer 52d, an upper surface of the second substrate layer 52b, and side surfaces of the first spacer layer 52c.

The second spacer layer 52e is interposed between the first and second solid electrolyte layers 52d, 52f. First and second diffusion rate-determining sections 56, 58 are also interposed between the first and second solid electrolyte layers 52d, 52f.

A first chamber 60 for adjusting the partial pressure of oxygen in a measurement gas is formed and comparted by a lower surface of the second solid electrolyte layer 52f, side surfaces of the first and second diffusion rate-determining sections 56, 58, and an upper surface of the first solid electrolyte layer 52d. A second chamber 62 for finely adjusting the partial pressure of oxygen in the measurement gas and measuring oxides such as nitrogen oxides (NOx) in the measurement gas is formed and comparted by a lower surface of the second solid electrolyte layer 52f, a side surface of the second diffusion rate-determining section 58, a side surface of the second spacer layer 52e, and an upper surface of the first solid electrolyte layer 52d.

The external space communicates with the first chamber 60 via the first diffusion-rate determining section 56, and the first chamber 60 communicates with the second chamber 62 via the second diffusion rate-determining section 58.

The first and second diffusion-rate determining sections 56, 58 give predetermined diffusion resistances to the measurement gas to be introduced into the first and second chambers 60, 62 respectively. Each of the first and second diffusion-rate determining sections 56, 58 can be formed as a passage composed of, for example, a porous material, or a small hole having a predetermined cross-sectional area so that the measurement gas may be introduced.

Especially, the second diffusion-rate determining section 58 is arranged and filled with a porous material comprising, for example, $ZrO_2$. It is preferable that the diffusion resistance of the second diffusion-rate determining section 58 is made larger than the diffusion resistance of the first diffusion-rate determining section 56. However, no problem occurs even when the former is smaller than the latter.

The atmosphere in the first chamber 60 is introduced into the second chamber 62 under the predetermined diffusion resistance via the second diffusion rate-determining section 58.

An inner pumping electrode 64 having a substantially rectangular planar configuration and composed of a porous cermet electrode is formed on an entire lower surface portion for forming the first chamber 60, of the lower surface of the second solid electrolyte layer 52f. An outer pumping electrode 66 is formed on a portion corresponding to the inner pumping electrode 64, of the upper surface of the second solid electrolyte layer 52f. An electrochemical pumping cell, i.e., a main pumping cell 68 is constructed by the inner pumping electrode 64, the outer pumping electrode 66, and the second solid electrolyte layer 52f interposed between the both electrodes 64, 66.

A desired control voltage (pumping voltage) Vp1 is applied between the inner pumping electrode 64 and the outer pumping electrode 66 of the main pumping cell 68 by the aid of an external variable power source 70 to allow a pumping current Ip1 to flow in a positive direction or in a negative direction between the outer pumping electrode 66 and the inner pumping electrode 64. Thus, the oxygen in the atmosphere in the first chamber 60 can be pumped out to the external space, or the oxygen in the external space can be pumped into the first chamber 60.

A reference electrode 74 is formed on a lower surface portion exposed to the reference gas-introducing space 54, of the lower surface of the first solid electrolyte layer 52d. An electrochemical sensor cell, i.e., a controlling oxygen partial pressure-detecting cell 76 is constructed by the inner pumping electrode 64, the reference electrode 74, the second solid electrolyte layer 52f, the second spacer layer 52e, and the first solid electrolyte layer 52d.

The controlling oxygen partial pressure-detecting cell 76 is operated such that the partial pressure of oxygen in the atmosphere in the first chamber 60 can be detected by using the electromotive force (voltage) V1 generated between the inner pumping electrode 64 and the reference electrode 74, on the basis of the difference in oxygen concentration between the atmosphere in the first chamber 60 and the reference gas (atmospheric air) in the reference gas-introducing space 54.

That is, the voltage V1, which is generated between the inner pumping electrode 64 and the reference electrode 74, is the electromotive force of the oxygen concentration cell generated on the basis of the difference between the partial pressure of oxygen of the reference gas introduced into the reference gas-introducing space 54 and the partial pressure of oxygen of the measurement gas in the first chamber 60. The voltage V1 has the following relationship known as the Nernst's equation.

$$V1 = RT/4F \cdot \ln(P1(O_2)/P0(O_2))$$

R: gas constant;
T: absolute temperature;
F: Faraday constant;
$P1(O_2)$: partial pressure of oxygen in the first chamber 60;
$P0(O_2)$: partial pressure of oxygen of the reference gas.

Therefore, the partial pressure of oxygen in the first chamber 60 can be detected by measuring the voltage V1 based on the Nernst's equation by using a voltmeter 78.

The detected value of the partial pressure of oxygen is used to control the pumping voltage Vp1 of the variable power source 70 by the aid of a feedback control system 80.

Specifically, the pumping operation effected by the main pumping cell 68 is controlled so that the partial pressure of oxygen in the atmosphere in the first chamber 60 has a predetermined value which is sufficiently low to make it possible to perform the control of the partial pressure of oxygen in the second chamber 62 in the next step.

Especially, in this embodiment, when the amount of oxygen pumped out by the main pumping cell 68 is changed, and the oxygen concentration in the first chamber 60 is changed, then the terminal voltage between the inner pumping electrode 64 and the reference electrode 74 of the main pumping cell 68 is changed without any time delay (the terminal voltage is changed in real time). Accordingly, it is possible to effectively suppress the oscillation phenomenon which would otherwise occur in the feedback control system 80.

The inner pumping electrode 64 and the outer pumping electrode 66 are composed of an inert material having a low catalytic activity on NOx such as NO contained in the measurement gas introduced into the first chamber 60. Specifically, the inner pumping electrode 64 and the outer pumping electrode 66 may be composed of a porous cermet electrode. In this embodiment, the electrodes are composed of a metal such as Pt and a ceramic such as $ZrO_2$. Especially, it is necessary to use a material which has a weak reducing ability or no reducing ability with respect to the NO component in the measurement gas, for the inner pumping electrode 64 disposed in the first chamber 60 to make contact with the measurement gas. It is preferable that the inner pumping electrode 64 is composed of, for example, a compound having the perovskite structure such as $La_3CuO_4$, a cermet comprising a ceramic and a metal such as Au having a low catalytic activity, or a cermet comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

In the gas sensor 50A according to the first embodiment, a detecting electrode 82 having a substantially rectangular planar configuration and composed of a porous cermet electrode is formed at a portion separated from the second diffusion rate-determining section 58, on an upper surface portion for forming the second chamber 62, of the upper surface of the first solid electrolyte layer 52*d*. An electrochemical pumping cell, i.e., a measuring pumping cell 84 is constructed by the detecting electrode 82, the reference electrode 74, and the first solid electrolyte layer 52*d*.

The detecting electrode 82 may be appropriately constructed by selecting a nitrogen oxide-decomposing catalyst, for example, an Rh cermet, a material having a low catalytic activity, or a nitrogen oxide-decomposing catalyst arranged in the vicinity of a material having a low catalytic activity. In the embodiment of the present invention, the detecting electrode 82 is composed of a porous cermet comprising Rh as a metal capable of reducing NOx as the objective gas component and zirconia as a ceramic.

Accordingly, NOx, which exists in the measurement gas introduced into the second chamber 62, is decomposed in accordance with the catalytic action of the detecting electrode 82. A constant voltage Vp2, which is at a level sufficient to pump out $O_2$ produced from NOx decomposed by the detecting electrode 82 toward the reference gas-introducing space 54, is applied between the detecting electrode 82 and the reference electrode 74 by the aid of a DC power source 86. The DC power source 86 is capable of applying a voltage having a magnitude to give a limiting current to the pumping operation for the oxygen produced during the decomposition effected by the measuring pumping cell 84.

Therefore, a pumping current Ip2 is allowed to flow through the measuring pumping cell 84 corresponding to the amount of oxygen pumped out by the pumping operation effected by the measuring pumping cell 84. The pumping current Ip2 is detected by an ammeter 88.

A pumping voltage sufficient to decompose NOx is applied between the detecting electrode 82 and the reference electrode 74, or an oxide-decomposing catalyst for decomposing NOx is arranged in the second chamber 62 so that $O_2$ produced in accordance with the action of the pumping voltage and/or the oxide-decomposing catalyst may be pumped out from the second chamber 62 by the aid of a predetermined pumping voltage.

On the other hand, an auxiliary pumping electrode 90 having a substantially rectangular planar configuration and composed of a porous cermet electrode is formed on an entire lower surface portion for forming the second chamber 62, of the lower surface of the second solid electrolyte layer 52*f*. An auxiliary electrochemical pumping cell, i.e., an auxiliary pumping cell 92 is constructed by the auxiliary pumping electrode 90, the second solid electrolyte layer 52*f*, the second spacer layer 52*e*, the first solid electrolyte layer 52*d*, and the reference electrode 74.

In the same manner as in the inner pumping electrode 64 of the main pumping cell 68 described above, the auxiliary pumping electrode 90 is based on the use of a material which has a weak reducing ability or no reducing ability with respect to the NO component in the measurement gas. In this embodiment, for example, the auxiliary pumping electrode 90 is preferably composed of a compound having the perovskite structure such as $La_3CuO_4$, a cermet comprising a ceramic and a metal such as Au having a low catalytic activity, or a cermet comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

A desired constant voltage Vp3 is applied between the auxiliary pumping electrode 90 and the reference electrode 74 of the auxiliary pumping cell 92 by the aid of an external DC power source 94. Thus, the oxygen in the atmosphere in the second chamber 62 can be pumped out to the reference gas-introducing space 54.

Accordingly, the partial pressure of oxygen in the atmosphere in the second chamber 62 is controlled to have a low value of partial pressure of oxygen which does not substantially affects the measurement for the amount of the objective component under a condition in which the measurement gas component (NOx) is not substantially reduced or decomposed. In this arrangement, the change in amount of oxygen introduced into the second chamber 62 is greatly reduced as compared with the change in the measurement gas, owing to the operation of the main pumping cell 68 for the first chamber 60. Accordingly, the partial pressure of oxygen in the second chamber 62 is controlled accurately and constantly.

Therefore, in the gas sensor 50A according to the first embodiment constructed as described above, the measurement gas, which is controlled for the partial pressure of oxygen in the second chamber 62, is introduced into the detecting electrode 82.

When it is intended to control the partial pressure of oxygen in the atmosphere in the first chamber 60 to have a low value of the partial pressure of oxygen which does not substantially affect the measurement of NOx, by operating the main pumping cell 68, in other words, when the pumping voltage Vp1 of the variable power source 70 is adjusted by the aid of the feedback control system 80 so that the voltage V1 detected by the controlling oxygen partial pressure-detecting cell 76 is constant, if the oxygen concentration in the measurement gas greatly changes, for example, in a range of 0 to 20%, then the respective partial pressures of oxygen in the atmosphere in the second chamber 62 and in the atmosphere in the vicinity of the detecting electrode 82 slightly change in ordinary cases. This phenomenon is caused probably because of the following reason. That is, when the oxygen concentration in the measurement gas increases, the distribution of the oxygen concentration occurs in the widthwise direction and the thickness direction in the first chamber 60. The distribution of the oxygen concentration changes depending on the oxygen concentration in the measurement gas.

However, in the case of the gas sensor 50A according to the first embodiment, the auxiliary pumping cell 92 is provided for the second chamber 62 so that the partial pressure of oxygen in its internal atmosphere always has a constant low value of the partial pressure of oxygen. Accordingly, even when the partial pressure of oxygen in the atmosphere introduced from the first chamber 60 into the second chamber 62 changes depending on the oxygen concentration in the measurement gas, the partial pressure of oxygen in the atmosphere in the second chamber 62 can be always made to have a constant low value, owing to the pumping operation performed by the auxiliary pumping cell 92. As a result, the partial pressure of oxygen can be controlled to have a low value at which the measurement of NOx is not substantially affected.

NOx in the measurement gas introduced into the detecting electrode 82 is reduced or decomposed around the detecting electrode 82. Thus, for example, a reaction of NO→½N$_2$+½O$_2$ is allowed to occur. In this process, a predetermined voltage Vp2, for example, 430 mV (700° C.) is applied between the detecting electrode 82 and the reference electrode 74 for constructing the measuring pumping cell 84, in a direction to pump out the oxygen from the second chamber 62 to the reference gas-introducing space 54.

Therefore, the pumping current Ip2 flowing through the measuring pumping cell 84 has a value which is proportional to a sum of the oxygen concentration in the atmosphere introduced into the second chamber 62, i.e., the oxygen concentration in the second chamber 62 and the oxygen concentration produced by reduction or decomposition of NOx by the aid of the detecting electrode 82.

In this embodiment, the oxygen concentration in the atmosphere in the second chamber 62 is controlled to be constant by means of the auxiliary pumping cell 92. Accordingly, the pumping current Ip2 flowing through the measuring pumping cell 84 is proportional to the NOx concentration. Further, the NOx concentration corresponds to the amount of diffusion of NOx. Therefore, even when the oxygen concentration in the measurement gas greatly changes, it is possible to accurately measure the NOx concentration, based on the use of the measuring pumping cell 84 by the aid of the ammeter 88.

It is assumed, for example, that the partial pressure of oxygen in the atmosphere in the second chamber 62 controlled by the auxiliary pumping cell 92 is 0.02 ppm, and the concentration of NO as the NOx component in the measurement gas is 100 ppm. The pumping current Ip2 flows in an amount corresponding to a sum (=50.02 ppm) of an oxygen concentration of 50 ppm produced by reduction or decomposition of NO and the oxygen concentration of 0.02 ppm in the atmosphere in the second chamber 62. Therefore, almost all of the pumping current value Ip2 obtained by operating the measuring pumping cell 84 represents the amount brought about by the reduction or decomposition of NO. Accordingly, the obtained result does not depend on the oxygen concentration in the measurement gas.

As shown in FIG. 1, the gas sensor 50A according to the first embodiment further comprises a heater 96 for generating heat in accordance with electric power supply from the outside. The heater 96 is embedded in a form of being vertically interposed between the first and second substrate layers 52a, 52b. The heater 96 is provided in order to increase the conductivity of oxygen ion. An insulative layer 98 composed of alumina or the like is formed to cover upper and lower surfaces of the heater 96 so that the heater 96 is electrically insulated from the first and second substrate layers 52a, 52b.

The heater 96 is arranged over the entire portion ranging from the first chamber 60 to the second chamber 62. Accordingly, each of the first chamber 60 and the second chamber 62 is heated to a predetermined temperature. Simultaneously, each of the main pumping cell 68, the controlling oxygen partial pressure-detecting cell 76, and the measuring pumping cell 84 is also heated to a predetermined temperature and maintained at that temperature.

Figure 2:
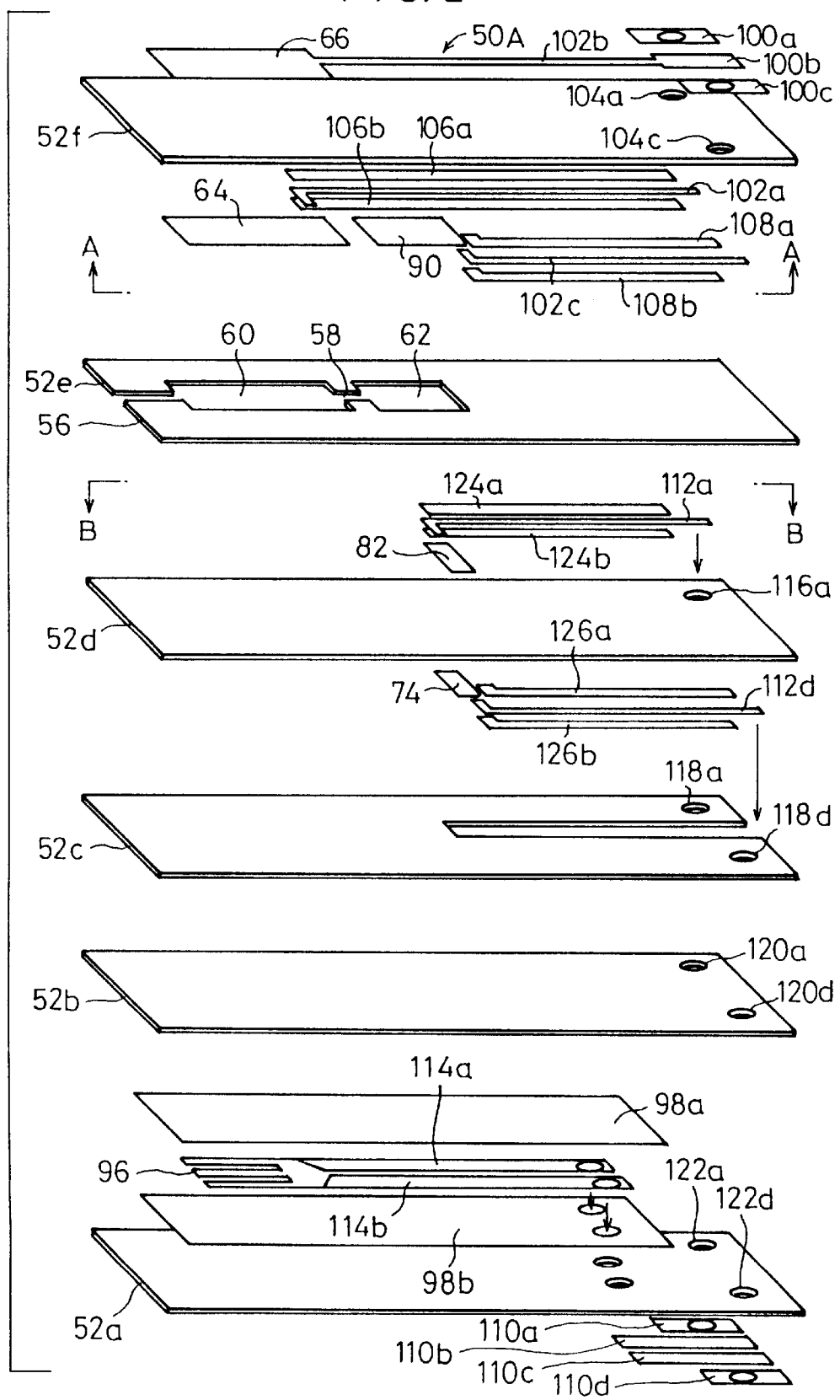
FIG. 2 shows an exploded perspective view illustrating the arrangement of the gas sensor according to the first embodiment.
Figure 3:
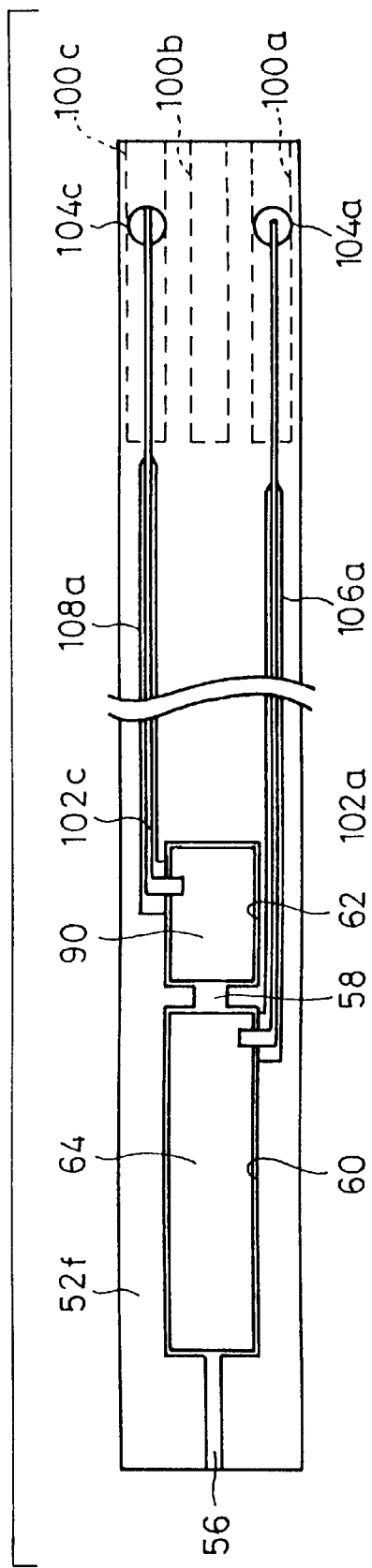
FIG. 3 shows a plan view taken along a line A—A shown in FIG. 2.
Figure 4:
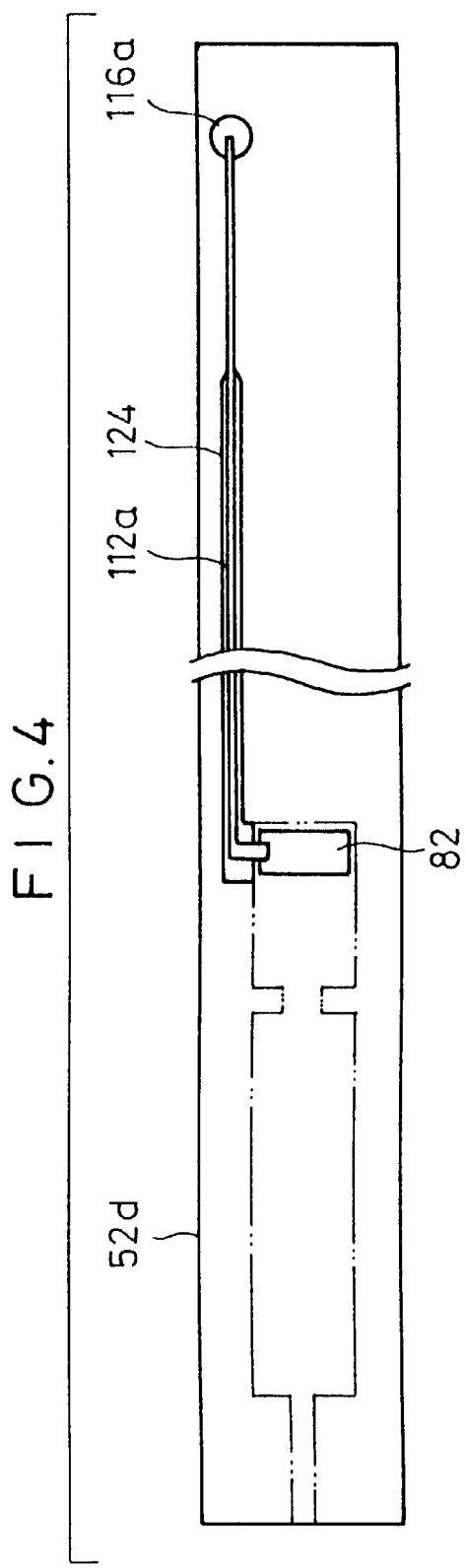
FIG. 4 shows a plan view taken along a line B—B shown in FIG. 2.

As shown in FIGS. 2 to 4, connector electrodes 100a to 100c are arranged on the upper surface of the second solid electrolyte layer 52f of the gas sensor 50A according to the first embodiment. The inner pumping electrode 64, the outer pumping electrode 66, and the auxiliary pumping electrode 90 are connected to the connector electrodes 100a to 100c via lead wires 102a to 102c respectively.

The lead wire 102b, which connects the outer pumping electrode 66 to the connector electrode 100b, is arranged on the second solid electrolyte layer 52f. The lead wires 102a, 102c are electrically connected to the connector electrodes 100a, 100c via through-holes 104a, 104c respectively.

The lead wires 102a to 102c described above are arranged as follows. That is, insulative layers 106 (upper insulative layer 106a, lower insulative layer 106b) and insulative layers 108 (upper insulative layer 108a, lower insulative layer 108b) are formed over and under the respective lead wires 102a, 102c which are formed under the second solid electrolyte layer 52f. Each of the lead wires 102a, 102c is in a state of being vertically interposed by the upper insulative layer (106a, 108a) and the lower insulative layer (106b, 108b).

Connector electrodes 110a to 110d are arranged on the lower surface of the first substrate layer 52a of the gas sensor 50A according to the first embodiment. The connector electrodes 110a to 110d are arranged as follows. That is, the detecting electrode 82 and the reference electrode 74 are connected to the connector electrodes 110a, 110d disposed on the outer side, via lead wires 112a, 112d respectively. A lead wire on the positive side 114a and a lead wire 114b on the negative side, which are wired from the heater 96, are connected to the connector electrodes 110b, 110c respectively.

The lead wire 112a, which connects the detecting electrode 82 to the connector electrode 110a, is electrically connected via respective through-holes 116a, 118a, 120a, 122a provided through the first solid electrolyte layer 52d, the first spacer layer 52c, and the first and second substrate layers 52a, 52b. The lead wire 112d, which connects the reference electrode 74 to the connector electrode 110d, is electrically connected via respective through-holes 118*d*, 120*d*, 122*d* provided through the first spacer layer 52*c* and the first and second substrate layers 52*a*, 52*b*.

The lead wires 112*a*, 112*d*, 114*a*, 114*b* described above are formed as follows. That is, insulative layers 124 (upper insulative layer 124*a*, lower insulative layer 124*b*) and insulative layers 126 (upper insulative layer 126*a*, lower insulative layer 126*b*) are formed over and under the respective lead wires 112*a*, 112*d* which are formed on the upper and lower surfaces of the first solid electrolyte layer 52*d*. Each of the lead wires 112*a*, 112*d* is in a state of being vertically interposed between the upper insulative layer (124*a*, 126*a*) and the lower insulative layer (124*b*, 126*b*).

In the gas sensor 50A according to the first embodiment, the insulative layers 106, 108, 124, 126 are provided at the positions corresponding to portions at which the temperature of the oxygen ion-conductive solid electrolyte is increased by heat generation effected by the heater 96, concerning the respective lead wires 102*a*, 102*c*, 112*a*, 112*d*.

Specifically, as shown in FIGS. 3 and 4, each of the insulative layers 106, 108, 124, 126 has a pattern in which one end is exposed to the first chamber 60 or the second chamber 62, and the other ends terminates at a position separated from the corresponding through-hole 104*a*, 104*c*, 116*a*, 118*d* by a predetermined distance.

In this embodiment, a portion of each of the lead wires 102*a*, 102*c*, 112*a*, 112*d*, which ranges from an end of the insulative layer 106, 108, 124, 126 on a side of the connector to each of the corresponding through-holes 104*a*, 104*c*, 116*a*, 118*d* (portion on which the insulative layer 106, 108, 124, 126 is not formed), is interposed by the same solid electrolyte as that used for the substrate. Thus, it is possible to more appropriately avoid invasion of $O_2$ from the outside.

As a result, the oxide can be measured highly accurately by the aid of the measuring pumping cell 84 provided for the second chamber 62.

Further, the gas sensor 50A according to the first embodiment is constructed by densifying at least the lead wires 102*c*, 112*a* which lead to the auxiliary pumping electrode 90 and the detecting electrode 82. Of course, the lead wires 102*a*, 112*d*, which lead to the inner pumping electrode 64 and the reference electrode 74, may be densified.

The densification of the lead wire 102*a*, 102*c*, 112*a*, 112*d* can be achieved by sintering the ceramic component for forming the backbone of the cermet in a degree equivalent to or superior to that of the substrate (solid electrolyte substrate). In this embodiment, the porosity of the lead wire 102*a*, 102*c*, 112*a*, 112*d* is preferably not more than 10%, and more preferably not more than 5%. Especially, when $ZrO_2$ is used as the ceramic component, the object can be achieved by using a material having a particle diameter which is finer than that used for the solid electrolyte substrate, using a material added with a smaller amount of $Y_2O_3$, or decreasing the content of $ZrO_2$ contained in the paste.

The gas sensor 50A according to the first embodiment is basically constructed as described above. Next, its function and effect will be explained.

Prior to the measurement of the oxide, the gas sensor 50A is set to be in a state in which the measurement gas can be introduced into the first chamber 60. Subsequently, an electric power is applied to the heater 96 to activate the first and second solid electrolyte layers 52*d*, 52*f* to be in a desired state.

Next, the measurement gas is introduced into the gas sensor 50A having been set as described above to start measurement of the oxide contained in the measurement gas.

The measurement gas is introduced into the first chamber 60 under the predetermined diffusion resistance through the first diffusion rate-determining section 56. The partial pressure of oxygen contained in the measurement gas is controlled to have a predetermined value in accordance with the predetermined pumping voltage Vp1 applied between the inner pumping electrode 64 and the outer pumping electrode 66 by the aid of the variable power source 70. That is, the partial pressure of oxygen in the first chamber 60 can be measured on the basis of the voltage V1 between the inner pumping electrode 64 and the reference electrode 74 detected by the voltmeter 78. The voltage V1 is the electromotive force of the oxygen concentration cell specified by the Nernst's equation described above. The voltage of the variable power source 70 is controlled so that the voltage V1 is, for example, not more than 350 mV. Thus, the partial pressure of oxygen in the first chamber 60 is controlled to have a predetermined value.

The measurement gas, which has been controlled to have the predetermined partial pressure of oxygen in the first chamber 60, is introduced into the second chamber 62 through the second diffusion rate-determining section 58 which is set to have a diffusion resistance larger than that of the first diffusion rate-determining section 56.

In the second chamber 62, the predetermined pumping voltage Vp2, which makes it possible to sufficiently pump out $O_2$ in the second chamber 62, is applied between the reference electrode 74 and the detecting electrode 82 by the aid of the DC power source 86. The oxide contained in the measurement gas is decomposed by the aid of the pumping voltage Vp2 or the oxide-decomposing catalyst arranged in the second chamber 62. $O_2$ generated thereby is pumped out toward the reference gas-introducing space 54 through the first solid electrolyte layer 52*d*. During this process, the current value Ip2, which is generated by the movement of oxygen ion, is measured by the ammeter 88. The concentration of the predetermined oxide, for example, NOx such as NO and $NO_2$ contained in the measurement gas is measured from the current value Ip2.

As described above, in the gas sensor 50A according to the first embodiment, the end on the side of the connector electrode of the insulative layer 106, 108, 124, 126 for covering each of the lead wires 102*a*, 102*c*, 112*a*, 112*d* is separated from the corresponding through-hole 104*a*, 104*c*, 116*a*, 118*d* by the predetermined distance. Further, at least the lead wires 102*c*, 112*a*, which lead to the auxiliary pumping electrode 90 and the detecting electrode 82, are densified. Accordingly, it is possible to appropriately avoid invasion of oxygen from the outside. Thus, the amount of the oxide can be measured highly accurately by using the measuring pumping cell 84.

In the gas sensor 50A according to the first embodiment, the respective insulative layers 106, 108, 124, 126 may be densified. In this case, it is possible for the respective insulative layers 106, 108, 124, 126 to select and use a material having a small porosity, preferably a material having a porosity of not more than 10%, from insulative materials such as alumina and spinel.

An illustrative experiment (hereinafter conveniently referred to as "first illustrative experiment") will now be described. Samples used in the first illustrative experiment were basically prepared as follows. That is, $ZrO_2$ powder added with 4 mol % of a stabilizer $Y_2O_3$ was shaped into a form of tape to obtained ceramic green sheets. Patterns of, for example, electrodes, lead wires, and insulative layers were formed, for example, by means of screen printing on the obtained ceramic green sheets. After completion of the pattern printing, the ceramic green sheets were stacked and integrated into one unit. After that, the stacked product was cut and divided into respective elements, followed by sintering to assembly the respective elements into a sensor.

In the case of a first sample (Comparative Example), the same paste as that used for the auxiliary pumping electrode 90 was used for the lead wire 102c connected to the auxiliary pumping electrode 90, which was prepared in a ratio of Pt—Au alloy (Au=1%)/$ZrO_2$=60/40% by volume. In this case, $ZrO_2$ was subjected to calcination to lower the sintering degree as compared with $ZrO_2$ used for the solid electrolyte substrate.

The detecting electrode 82 was prepared in a ratio of Rh/$ZrO_2$=60/40% by volume. In this case, $ZrO_2$ was also subjected to calcination to lower the sintering degree as compared with $ZrO_2$ used for the solid electrolyte substrate. On the other hand, the lead wire 112a connected to the detecting electrode 82 was prepared in a ratio of Pt/$ZrO_2$=60/40% by volume. In this case, $ZrO_2$ was also subjected to calcination to lower the sintering degree as compared with $ZrO_2$ used for the solid electrolyte substrate.

In the case of a second sample (Example 1), a densified paste was used for the lead wire 102c connected to the auxiliary pumping electrode 90, which was prepared in a ratio of Pt—Au alloy (Au=1%)/$ZrO_2$=60/40% by volume. In this case, the same $ZrO_2$ as that for the ceramic green sheet for constructing the substrate was used.

The detecting electrode 82 was prepared in a ratio of Rh/$ZrO_2$=60/40% by volume. In this case, $ZrO_2$ was also subjected to calcination to lower the sintering degree as compared with $ZrO_2$ used for the solid electrolyte substrate. On the other hand, the lead wire 112a connected to the detecting electrode 82 was prepared in a ratio of Pt/$ZrO_2$=60/40% by volume. In this case, the same $ZrO_2$ as that for the ceramic green sheet for constructing the substrate was used.

In the case of a third sample (Example 2), densified $Al_2O_3$ was used for the insulative layers 106, 108, 124, 126 for the respective lead wires 102a, 102c, 112a, 112d, in addition to the same condition as that used for Example 1.

The first illustrative experiment was performed by using Comparative Example, Example 1, and Example 2 to observe the relationship between the concentration of NO contained in the measurement gas and the current value Ip2 measured by the ammeter 88 connected between the detecting electrode 82 and the reference electrode 74 of the measuring pumping cell 84. Experimental results obtained in the first illustrative experiment are shown in FIG. 5.

Figure 5:
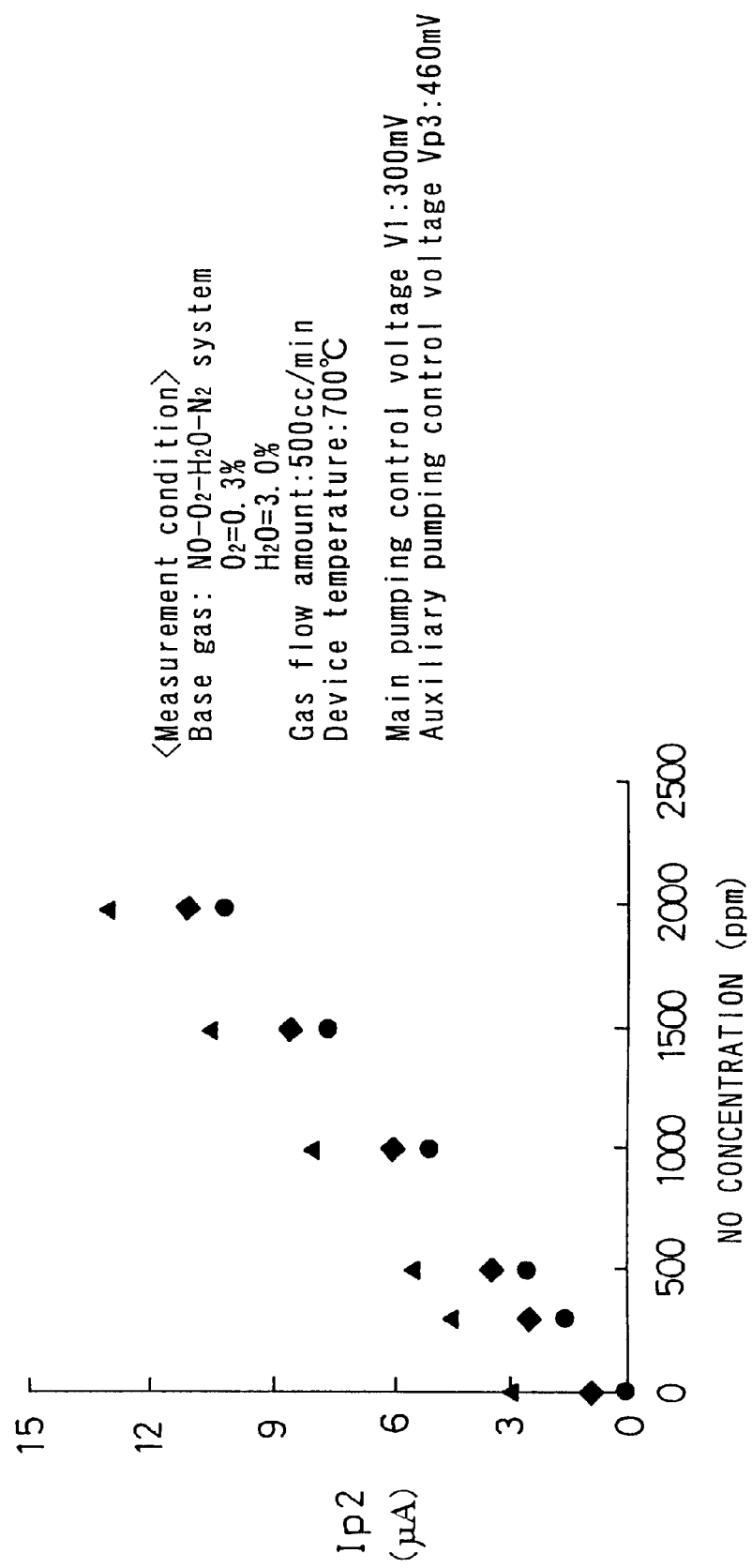
FIG. 5 shows experimental results obtained in a first illustrative experiment, illustrating characteristics to depict the relationship between the concentration of NO contained in a measurement gas and the pumping current Ip2 flowing through a measuring pumping cell.

In FIG. 5, a characteristic indicated by solid triangles represents the experimental result obtained for Comparative Example. A characteristic indicated by solid diamonds represents the experimental result obtained for Example 1. A characteristic indicated by solid circles represents the experimental result obtained for Example 2. According to the experimental results shown in FIG. 5, the offset of the pumping current Ip2 flowing through the measuring pumping cell 84 can be decreased by densifying at least the lead wires 102c, 112a (see the characteristic concerning Example 1). Further, the offset can be made approximately zero by making combination with the dense insulative layers 108, 124 (see the characteristic concerning Example 2).

That is, the ends on the side of the connectors of the insulative layers 106, 126 formed for the inner pumping electrode 64 and the reference electrode 74 respectively are separated by the predetermined distance from the corresponding through-holes 104a, 118d. Further, the lead wires 102a, 112d connected to the electrodes 64, 74 are densified. Thus, it is possible to effectively avoid invasion of oxygen from the outside into the first chamber 60, and it is possible to highly accurately control the oxygen concentration in the first chamber 60 to be the predetermined concentration.

As for the process in which the measurement gas having been highly accurately adjusted for the oxygen concentration is introduced into the second chamber 62, the second chamber 62 is constructed such that the ends on the side of the connectors of the insulative layers 108, 124 formed for the auxiliary pumping electrode 90 and the detecting electrode 82 respectively are separated by the predetermined distance from the corresponding through-holes 104c, 116a, and the lead wires 102c, 112a connected to the electrodes 90, 82 are densified, in the same manner as described above. Thus, invasion of oxygen from the outside into the second chamber 62 is avoided. Accordingly, it is possible to highly accurately measure the concentration of the oxide in accordance with $O_2$ obtained from only the oxide contained in the measurement gas.

It is desirable that the porosity of the cermet material for constructing the lead wires 102a, 102c, 112a, 112d is not more than 10%, and more preferably not more than 5% as described above. The porosity can be determined, for example, from SEM image (cross-sectional image obtained by using an electron microscope) of mirror-finished surface. That is, the relationship is expressed by the following expression provided that the easiness for $O_2$ to invade into a substance is represented by 1/R.

$$1/R = \rho \cdot S/L$$

ρ: porosity (−)
S: cross-sectional area of lead wire (mm²)
L: length of lead wire (mm)

Figure 6:
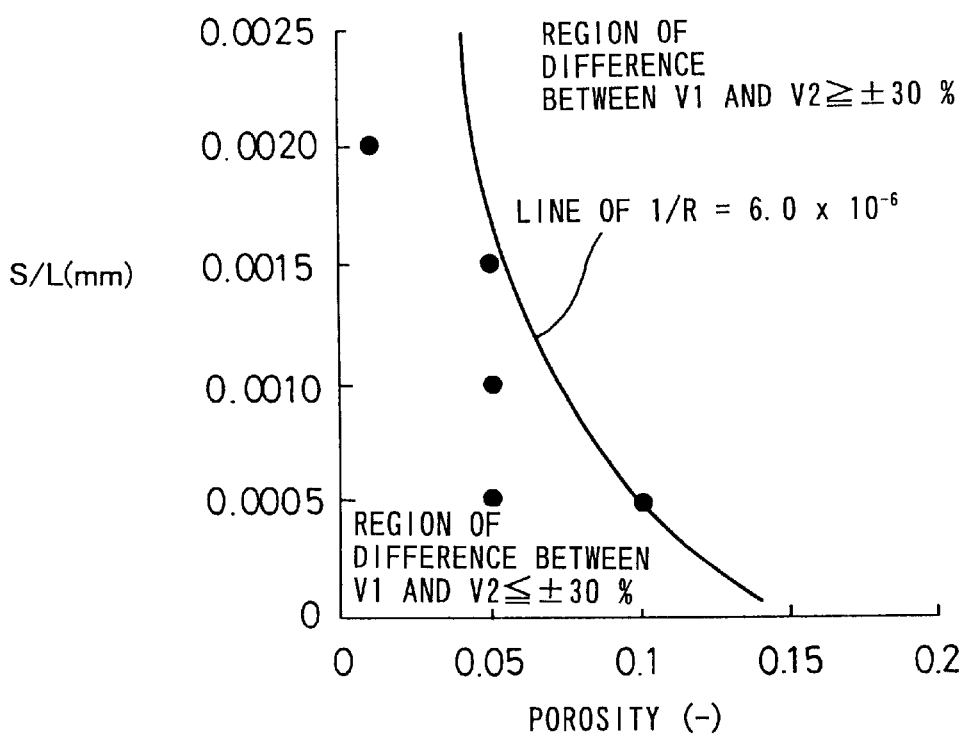
FIG. 6 illustrates the relation exhibiting the easiness for oxygen to invade the substance in relation to the porosity of the insulative material.

On this assumption, in consideration of the relationship between the electromotive force V1 of the oxygen concentration cell generated by the difference between the partial pressure of oxygen in the first chamber 60 and the partial pressure of oxygen in the reference gas-introducing space 54 and the electromotive force V2 of the oxygen concentration cell generated by the difference between the partial pressure of oxygen in the second chamber 62 and the partial pressure of oxygen in the reference gas-introducing space 54, it has been found that the relationship between the electromotive forces V1 and V2 approaches an ideal state in a region of $(1/R) \leq 6.0 \times 10^{-6}$ as shown in FIG. 6. It is understood that when the porosity is appropriately selected by using the factor of S/L on the basis of the concept described above, the invasion of $O_2$ from those other than the first and second diffusion rate-determining sections 56, 58 can be controlled to be at a predetermined value at which the measurement is not affected. Further, considering, for example, the coefficient of contraction of the substrate and the lead wire during sintering and the shape of the gas sensor 50A, it is preferable that the porosity is not more than 10%. That is, the degree of freedom of design is increased for the width and the thickness with respect to the length of the lead wire. When the porosity is not more than 5%, the degree of freedom of design is further increased, which is preferred.

The relationship between the electromotive forces V1 and V2 can be allowed to further approach the ideal state by densifying the insulative layers 106, 108, 124, 126 for the lead wires 102a, 102c, 112a, 112d.

It is noted that the gas sensor 50A according to the first embodiment can be also applied to a sensor for highly accurately measuring the amount of inflammable gases such as $H_2$, CO, and hydrocarbon contained in a measurement gas.

In the case of such application, concerning the first embodiment described above, the pumping voltage Vp1 is controlled by the aid of the feedback control system 80 so that the electromotive force V1 of the oxygen concentration cell measured by the voltmeter 78 is, for example, 930 mV between the inner pumping electrode 64 and the outer pumping electrode 66 provided for the first chamber 60. Accordingly, the oxygen concentration in the first chamber 60 is adjusted to be a concentration at which the inflammable gas does not burn.

The measurement gas, which has been adjusted for the oxygen concentration to be the predetermined concentration by the aid of the main pumping cell 68, is introduced into the second chamber 62 through the second diffusion rate-determining section 58. In the second chamber 62, the voltage of the DC power source 86 is controlled so that the partial pressure of oxygen corresponds to, for example, 450 mV which is obtained after conversion and calculation as the electromotive force of the oxygen concentration cell. It is assumed that no oxide-decomposing catalyst is arranged in the second chamber 62.

In this state, the inflammable gas contained in the measurement gas introduced into the second chamber 62 is combined with $O_2$ pumped into from the outside by the aid of the pumping voltage Vp2 applied to the detecting electrode 82. At this time, the pumping current Ip2 flowing through the ammeter 88 is detected, and thus the amount of the inflammable gas can be measured.

Next, explanation will be made for a gas sensor 50B according to a second embodiment with reference to FIG. 7. Components or parts corresponding to those shown in FIG. 1 are designated by the same reference numerals, duplicate explanation of which will be omitted.

Figure 7:
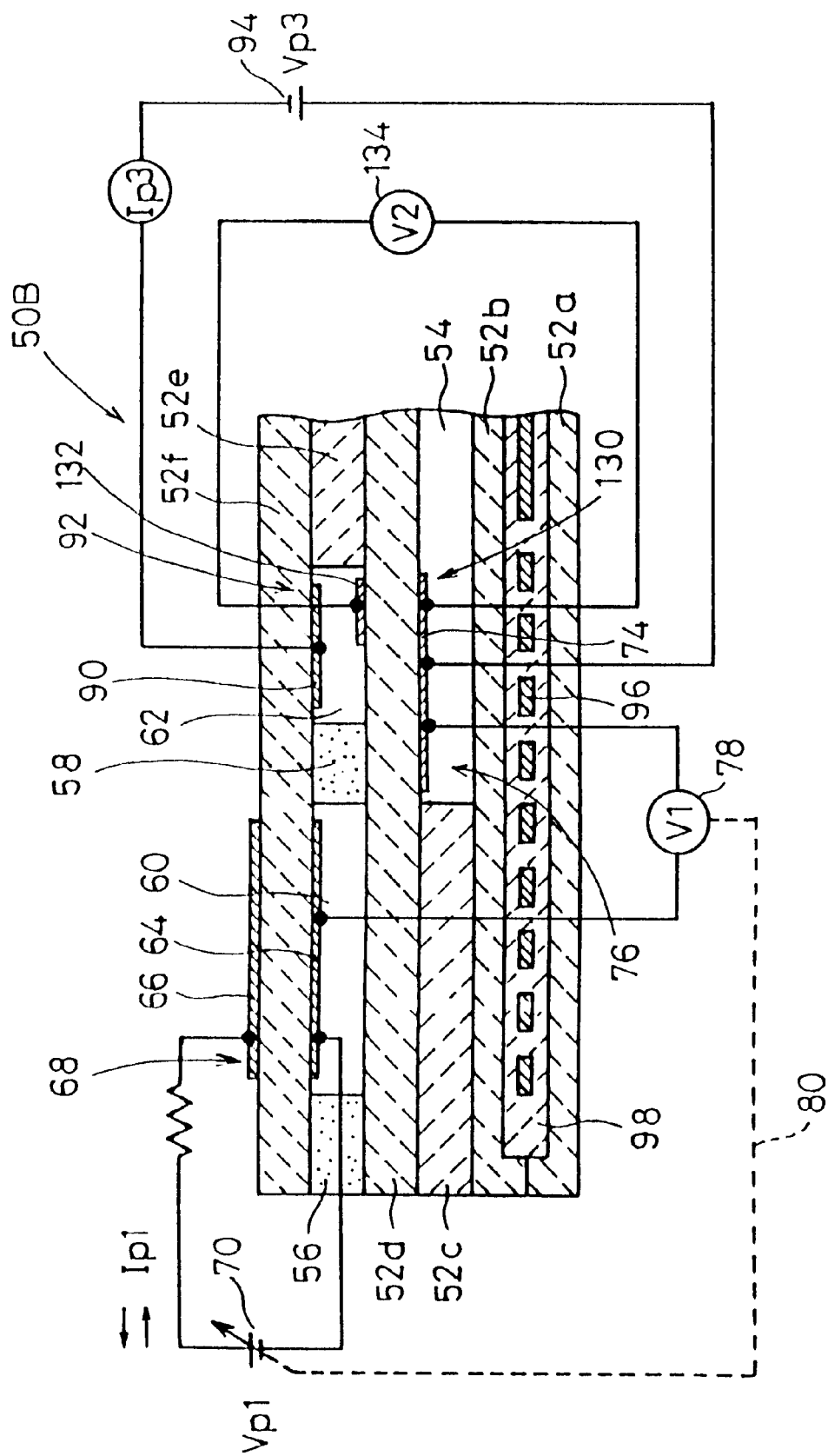
FIG. 7 shows a cross-sectional view illustrating an arrangement of a gas sensor according to a second embodiment.

As shown in FIG. 7, the gas sensor 50B according to the second embodiment is constructed in approximately the same manner as the gas sensor 50A according to the first embodiment (see FIG. 1). However, the former is different from the latter in that a measuring oxygen partial pressure-detecting cell 130 is provided instead of the measuring pumping cell 84.

The measuring oxygen partial pressure-detecting cell 130 comprises a detecting electrode 132 formed on an upper surface portion for forming the second chamber 62, of the upper surface of the first solid electrolyte layer 52d, a reference electrode 74 formed on the lower surface of the first solid electrolyte layer 52d, and the first solid electrolyte layer 52d.

In this embodiment, an electromotive force (electromotive force of an oxygen concentration cell) V2, which corresponds to the difference in oxygen concentration between an atmosphere around the detecting electrode 132 and an atmosphere around the reference electrode 74, is generated between the detecting electrode 132 and the reference electrode 74 of the measuring oxygen partial pressure-detecting cell 130.

Therefore, the partial pressure of oxygen in the atmosphere around the detecting electrode 132, in other words, the partial pressure of oxygen defined by oxygen produced by reduction or decomposition of a measurement gas component (NOx) is detected as a voltage value V2 by measuring the electromotive force (voltage) V2 generated between the detecting electrode 132 and the reference electrode 74 by using a voltmeter 134.

The principle of detection effected by the gas sensor 50B according to the second embodiment will be explained. At first, when the NO concentration in the external space is 0 ppm, the pumping voltage Vp1 of the main pumping cell 68 is controlled so that the partial pressure of oxygen in the atmosphere in the first chamber 60 is maintained at $1.3 \times 10^{-7}$ atm, i.e., the electromotive force V1=about 300 mV.

Next, the setting voltage Vp3 applied to the auxiliary pumping cell 92 is set to be 460 mV. The partial pressure of oxygen in the second chamber 62 is controlled to be $6.1 \times 10^{-11}$ atm owing to the action of the auxiliary pumping cell 92. As a result, the electromotive force V2 between the detecting electrode 132 and the reference electrode 74 in the measuring oxygen partial pressure-detecting cell 130 is about 460 mV.

In this case, even when the partial pressure of oxygen in the second chamber 62 is $1 \times 10^{-11}$ atm, then the inflammable gas component is oxidized in the first chamber 60, and the sensitivity to NOx is not affected, because the partial pressure of oxygen in the first chamber 60 is $1.3 \times 10^{-7}$ atm.

When the NOx concentration in the external space is gradually increased, then the reaction of reduction or decomposition of NOx is caused on the detecting electrode 132, and the oxygen concentration in the atmosphere around the detecting electrode 132 is increased, because the detecting electrode 132 also functions as a NOx-reducing catalyst in the same manner as the detecting electrode 82 in the measuring pumping cell 84 as described above (see FIG. 1). Accordingly, the electromotive force V2, which is generated between the detecting electrode 132 and the reference electrode 74, is gradually decreased. The degree of decrease in the electromotive force V2 represents the NO concentration. That is, the electromotive force V2, which is outputted from the measuring oxygen partial pressure-detecting cell 130 constructed by the detecting electrode 132, reference electrode 74, and the first solid electrolyte layer 52d, represents the NO concentration in the measurement gas.

Also in the gas sensor 50B according to the second embodiment, the end on the side of the connector electrode of the insulative layer 106, 108, 124, 126 for covering each of the lead wires 102a, 102c, 112a, 112d is separated by the predetermined distance from the corresponding through-hole 104a, 104c, 116a, 118d. Further, at least the lead wires 102c, 112a, which lead to the auxiliary pumping electrode 90 and the detecting electrode 82, are densified. Accordingly, it is possible to appropriately avoid invasion of oxygen from the outside. Thus, the amount of the oxide can be measured highly accurately by using the measuring oxygen partial pressure-detecting cell 130.

Two illustrative experiments (hereinafter conveniently referred to as "second and third illustrative experiments" respectively) will now be described. The illustrative experiments were also carried out by preparing the same samples as the first sample (Comparative Example), the second sample (Example 1), and the third sample (Example 2) used in the first illustrative experiment described above.

At first, the second illustrative experiment was performed by using Comparative Example, Example 1, and Example 2 to observe the relationship between the electromotive force V1 of the oxygen concentration cell generated between the inner pumping electrode 64 and the reference electrode 74 of the controlling oxygen partial pressure-detecting cell 76 and the electromotive force V2 of the oxygen concentration cell generated in this process between the detecting electrode 132 and the reference electrode 74 of the measuring oxygen partial pressuredetecting cell 130 provided for the second chamber 62. Experimental results obtained in the second illustrative experiment are shown in FIG. 8.

Figure 8:
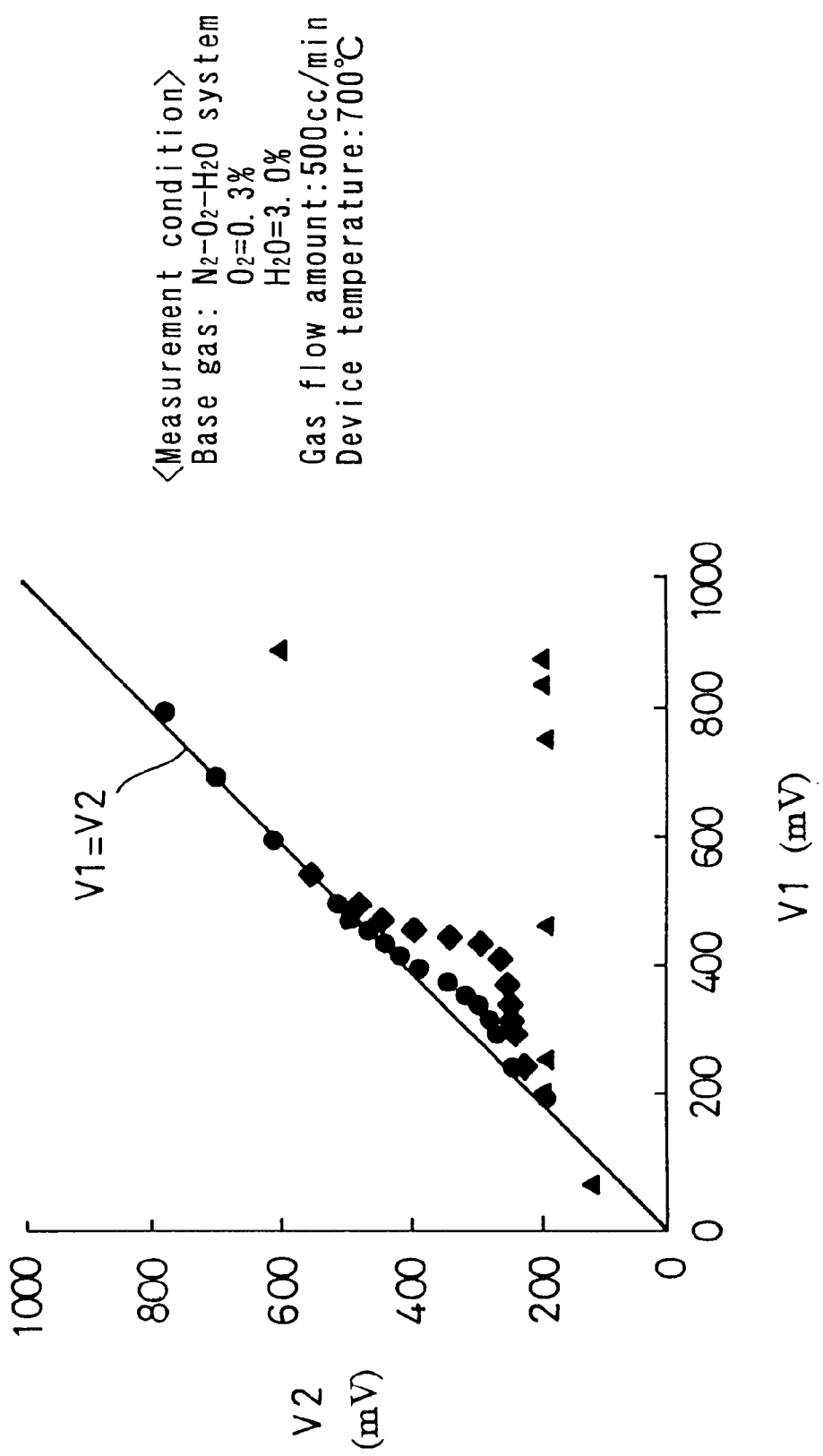
FIG. 8 shows experimental results obtained in a second illustrative experiment, illustrating characteristics to depict the relationship between the electromotive force V1 of the oxygen concentration cell generated in the controlling oxygen partial pressure-detecting cell and the electromotive force V2 of the oxygen concentration generated in the measuring oxygen partial pressure-detecting cell.

In FIG. 8, a characteristic indicated by solid triangles represents the experimental result obtained for Comparative Example. A characteristic indicated by solid diamonds represents the experimental result obtained for Example 1. A characteristic indicated by solid circles represents the experimental result obtained for Example 2. According to the experimental results shown in FIG. 8, it is understood that the partial pressure of oxygen in the second chamber 62 as the measuring space can be allowed to approach the ideal value (=control value for the first chamber 60 as the oxygen concentration-adjusting space) by densifying the lead wires 102a, 102c, 112a, 112d, and it is possible to highly accurately measure the oxide.

As shown in FIG. 6, also in the case of the gas sensor 50B according to the second embodiment, assuming that the easiness for $O_2$ to invade into a substance is represented by $1/R$, a good relationship has been found in which the difference between the electromotive force V1 of the oxygen concentration cell in the first chamber 60 and the electromotive force V2 of the oxygen concentration cell in the second chamber 62 is within ±30% in a range to give $(1/R) \leqq 6.0 \times 10^{-6}$. Therefore, also in the case of the gas sensor 50B according to the second embodiment, it has been found that a preferable result is obtained by allowing the porosity p to be not more than 10% by making appropriate selection while considering, for example, the factor of S/L, the coefficient of contraction of the substrate and the lead wire during sintering, and the shape of the gas sensor 50B.

In the third illustrative experiment, Comparative Example and Example 2 were prepared to observe the change in electromotive force V2 generated in the measuring oxygen partial pressure-detecting cell 130 when the NO concentration was changed in a range of 0 to 1000 ppm in a measurement gas comprising basic gas components based on the NO—$O_2$—$H_2O$—$N_2$ system.

In the third illustrative experiment, the pumping voltage Vp1 (equivalent to the electromotive force V1) of the main pumping cell 68 was 300 mV, and the auxiliary pumping voltage Vp3 of the auxiliary pumping cell 142 was 460 mV.

Figure 9:
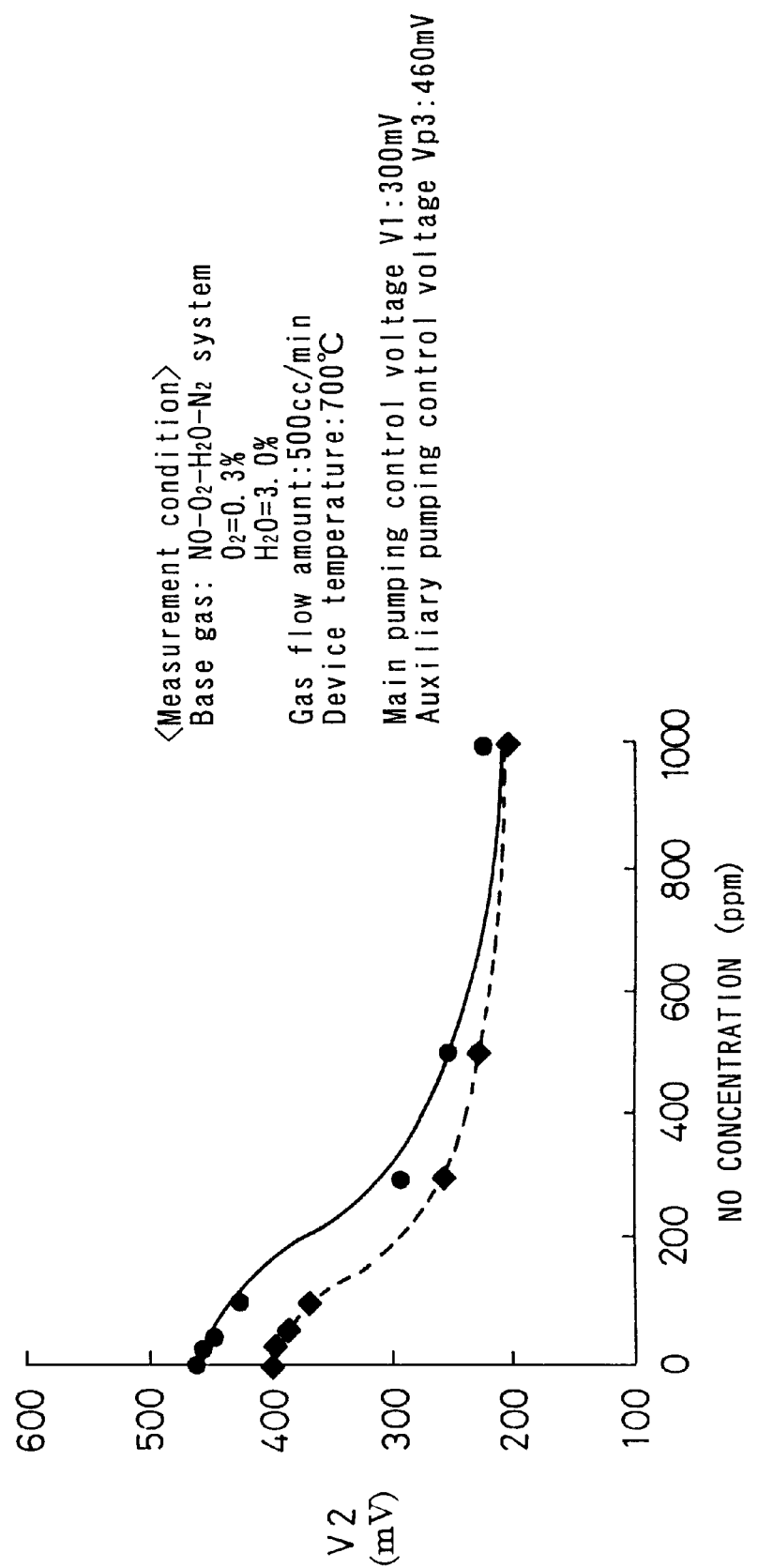
FIG. 9 shows experimental results obtained in the second illustrative experiment, illustrating characteristics to depict the change in electromotive force generated in the measuring oxygen partial pressure-detecting cell with respect to the change in NO concentration, together with those obtained for Comparative Example.
Figure 10:
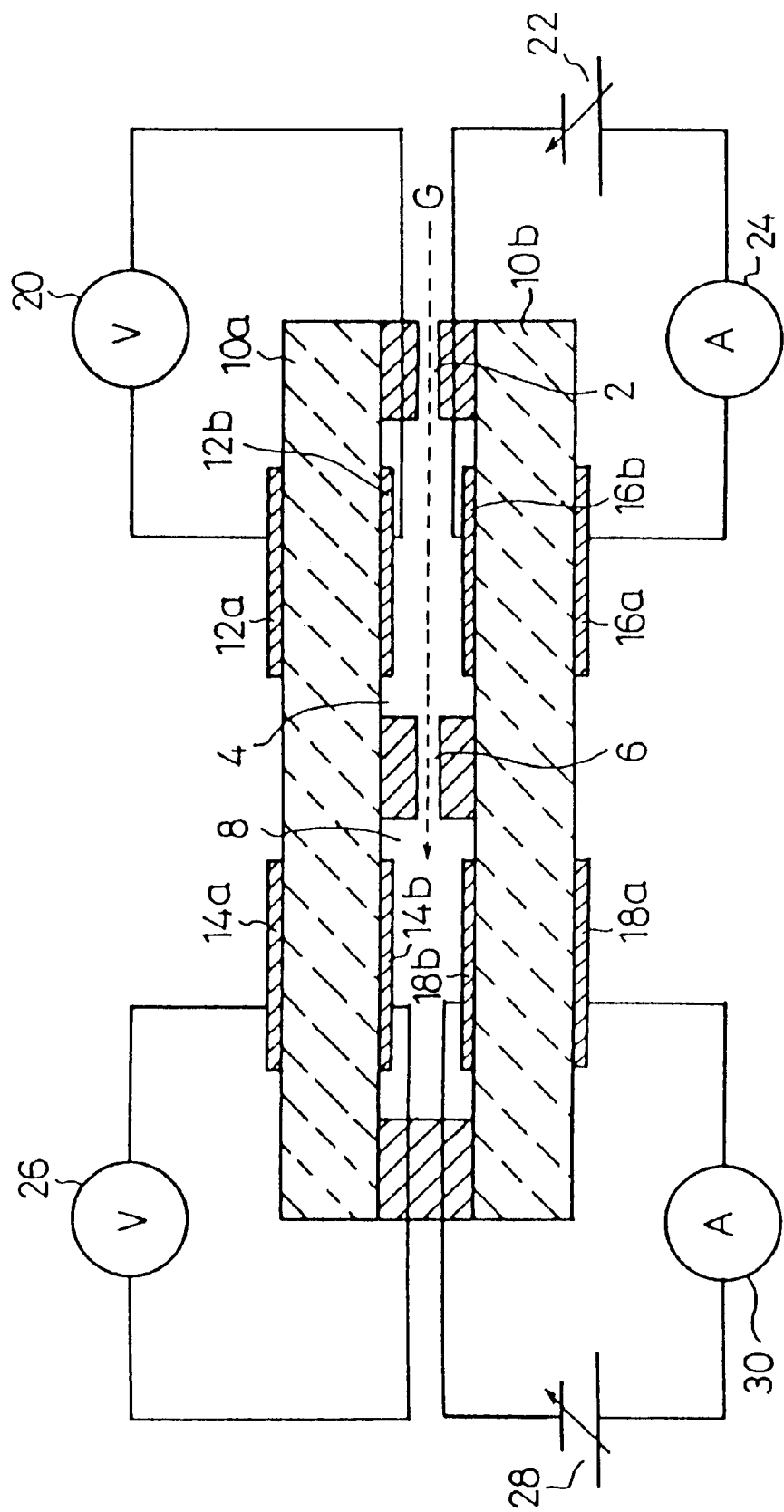
FIG. 10 shows a cross-sectional arrangement of the gas analyzer concerning the conventional technique.

Experimental results obtained in this illustrative experiment are shown in FIG. 9. In FIG. 9, a characteristic indicated by a solid line (indicated by solid circles) represents the experimental result obtained for Example 2. A characteristic indicated by a broken line (indicated by solid diamonds) represents the experimental result obtained for Comparative Example.

As clarified from the experimental results shown in FIG. 9, in Example 2, the electromotive force V2 at an NO concentration=0 ppm can be made to have a value higher than that obtained for Comparative Example, specifically a value which is approximately the same as the auxiliary pumping voltage value Vp3 as the value in the ideal state, and hence it is possible to increase the sensitivity (degree of decrease in electromotive force V2) at a low concentration, because the insulative layers 106, 108, 124, 126 as well as the lead wires 102a, 102c, 112a, 113d are densified.

Accordingly, when the NO component is contained in the measurement gas, the electromotive force V2 corresponding to the amount of NO is generated between the detecting electrode 132 and the reference electrode 74 for constructing the measuring oxygen partial pressure-detecting cell 130. Thus, the amount of NO can be accurately determined by detecting the electromotive force V2.

The gas sensor 50B according to the second embodiment can be also applied to a sensor for highly accurately measuring the amount of inflammable gases such as CO and hydrocarbon contained in a measurement gas, in the same manner as the gas sensor 50A according to the first embodiment.

The gas sensors 50A, 50B according to the first and second embodiments have been explained for the case in which only one second chamber 62 is connected to the first chamber 60. However, a plurality of second chambers 62 may be connected to the first chamber 60 to simultaneously measure a plurality of oxides of different types.

For example, a third chamber, which is constructed in the same manner as the second chamber 62, may be provided and connected in series to the second chamber 62 through a diffusion rate-determining section, and the second chamber 62 is provided, for example, with the measuring pumping cell. In this case, a pumping voltage, which is different from the pumping voltage Vp2 applied to the detecting electrode 82, is applied to a detecting electrode provided for the third chamber. Thus, it is possible to measure an oxide of a type different from that measured in the second chamber 62. Such an arrangement may be made equivalently when the measuring oxygen partial pressure-detecting cell is provided for the second chamber 62, in place of the measuring pumping cell as described above.

The oxides to be measured in the second and third chambers include, for example, NO, $NO_2$, $CO_2$, $H_2O$, and $SO_2$. Further, the third chamber may be connected in parallel to the second chamber.

The gas sensor according to the present invention is not limited to the embodiments described above. It is a matter of course that the gas sensor according to the present invention may be constructed in various forms without deviating from the gist or essential characteristics of the present invention.

What is claimed is:

1. A NOx gas sensor comprising:

a main pumping means including an inner pumping electrode and an outer pumping electrode arranged on inner and outer surfaces of an outer substrate composed of an oxygen ion-conductive solid electrolyte comprising $ZrO_2$, for pumping-processing oxygen contained in a measurement gas introduced from external space on the basis of a control voltage applied between said inner pumping electrode and said outer pumping electrode;

an auxiliary pumping means including an inner auxiliary electrode and an outer auxiliary electrode arranged on said inner and outer surfaces of said substrate composed of said oxygen ion-conductive solid electrolyte, for pumping-processing oxygen contained in said measurement gas after being pumping-processed by said main pumping means on the basis of an auxiliary pumping voltage applied between said inner auxiliary electrode and said outer auxiliary electrode;

an electric signal-generating conversion means including an inner detecting electrode and an outer detecting electrode arranged on inner and outer surfaces of an inner substrate composed of an oxygen ion-conductive solid electrolyte, said inner detecting electrode provided in a processing space, for decomposing a predetermined gas component contained in said measurement gas after being pumping-processed by said main pumping means, by means of a catalytic action and/or electrolysis to make conversion into an electric signal corresponding to an amount of oxygen produced by said decomposition; and insulative layers and conductive layers formed on a plurality of solid electrolyte green sheets comprising $ZrO_2$, said plurality of green sheets being stacked and integrated into one unit followed by being sintered to form said outer substrate and said inner substrate, wherein:

at least a lead wire connected to said inner detecting electrode of said electric signal-generating conversion means, which is exposed to said measurement gas introduced into said processing space, comprises a cermet comprising densified $ZrO_2$ and a metal of the platinum group, said $ZrO_2$ having a sintering degree not less than a sintering degree of $ZrO_2$ in said solid electrolyte substrate;

said densified lead wire having a porosity of not more than 10% whereby the ease of $O_2$ entry into the densified lead wire is represented by 1/R where $$1/R = (r)(S/L)$$

and r = porosity,
S = the cross-sectional area of the lead wire,
L = the length of the lead wire, and
wherein said ease of $O_2$ entry 1/R is less than or equal to $6.0 \times 10^{-6}$;

said densified lead wire has a covering of densified insulated material that surrounds the lead wire, which extends from the processing space where the detecting electrode is provided to a short, predetermined distance from the end of the lead wire, and which maintains said densified lead wire electrically insulated, said densified lead wire and surrounding densified insulated material being maintained between solid electrolyte sheets on either side of the densified lead wire; and said predetermined gas component contained in said measurement gas is measured on the basis of said electric signal detected by said electric signal-generating conversion means.

2. The gas sensor according to claim 1, wherein said electric signal-generating conversion means comprises:

a measuring pumping means including said inner detecting electrode and said outer detecting electrode arranged on said inner and outer surfaces of said substrate composed of said oxygen ion-conductive solid electrolyte, for decomposing said predetermined gas component contained in said measurement gas after being pumping-processed by said main pumping means, by means of said catalytic action and/or said electrolysis so that oxygen produced by said decomposition is pumping-processed on the basis of a measuring pumping voltage applied between said inner detecting electrode and said outer detecting electrode; and a current-detecting means for detecting a pumping current generated depending on an amount of said oxygen pumping-processed by said measuring pumping means, wherein:

said predetermined gas component contained in said measurement gas is measured on the basis of said pumping current detected by said current-detecting means.

3. The gas sensor according to claim 1, wherein said electric signal-generating conversion means comprises:

a concentration-detecting means including said inner detecting electrode and said outer detecting electrode arranged on said inner and outer surfaces of said substrate composed of said oxygen ion-conductive solid electrolyte, for decomposing said predetermined gas component contained in said measurement gas after being pumping-processed by said main pumping means, by means of said catalytic action to generate an electromotive force corresponding to a difference between an amount of oxygen produced by said decomposition and an amount of oxygen contained in a gas existing on a side of said outer detecting electrode; and a voltage-detecting means for detecting said electromotive force generated by said concentration-detecting means, wherein:

said predetermined gas component contained in said measurement gas is measured on the basis of said electromotive force detected by said voltage-detecting means.

* * * * *